United States Patent
Bonneville et al.

[11] Patent Number: 6,086,540
[45] Date of Patent: Jul. 11, 2000

[54] METHODS OF ULTRASOUND IMAGING USING ECHOGENICALLY PERSISTENT CONTRAST AGENTS

[75] Inventors: Daniel Aron Bonneville; Yigal Greener; Anne Louise Killam; Mary Therese Kuvelas, all of San Diego; Jeffrey John Miller, Encinitas, all of Calif.

[73] Assignee: Molecular Biosystems, Inc., San Diego, Calif.

[21] Appl. No.: 08/946,342

[22] Filed: Oct. 7, 1997

[51] Int. Cl.$^7$ ............................................. A61B 8/00
[52] U.S. Cl. ............................................. 600/458
[58] Field of Search ........................... 600/458, 454, 600/437, 441, 443, 447

[56] References Cited

U.S. PATENT DOCUMENTS

| | | | |
|---|---|---|---|
| 5,577,505 | 11/1996 | Brock-Fisher et al. | 600/458 |
| 5,694,937 | 12/1997 | Kamiyama | 600/458 |
| 5,735,281 | 4/1998 | Rafter et al. | 600/458 |
| 5,776,429 | 7/1998 | Unger et al. | 600/458 |
| 5,833,613 | 11/1998 | Averkiou et al. | 600/440 |

*Primary Examiner*—Francis J. Jaworski
*Assistant Examiner*—Ali M. Imam
*Attorney, Agent, or Firm*—Morrison & Foerster LLP

[57] ABSTRACT

The present invention relates to a method of imaging using multiple doses of an echogenically persistent contrast agent. In particular, it relates to the use of ultrasound energy to eliminate residual echogenicity attributed to the first dose of contrast agent prior to administering a second dose of contrast agent for the purpose of acquiring more images.

12 Claims, 2 Drawing Sheets

Flow Chart

Figure 1

Flow Chart

Optimize Baseline Ultrasound Cardiac Image Settings

Set power of output level to achieve no higher than 0.2 MI for 5 MHz or 0.1 MI for lower frequencies in B-mode. Then, using standard sonography technique optimize image at above power setting for gains etc. For transducer frequencies below 2.0 MHz, acoustic power output should be set as low as possible while still achieving cardiac visualization.

Deliver First Bolus Injection of Intravenous of Contrast Agent

For best results, the bolus dosage should be adjusted such that in the first minute (with or without attenuation) the gray scale enhancement of the myocardium is isodense with the left ventricular chamber density. Experience has shown that if the isodense condition is achieved at this stage, the resulting enhanced image is optimal for assessing myocardial perfusion status.

Wait for Ventricular Chamber to Clear of Contrast

Time is dependent on dose and agent but for a 0.5 mL bolus of albumin microspheres containing perfluoropentane or perfluorohexane, time is about 4 minutes. Record Perfusion status of the myocardium using densitometry or visual assessment. The resulting image should show an enhanced myocardium (bright gray) with a dark ventricular chamber.

Increase Power output to MI 0.6 or Higher for All Frequencies (in B-mode)

Watch myocardial gray scale return to baseline (Color Doppler may also be initiated and swept across image field to speed process). This will return the myocardial enhancement of baseline allowing for an accurate assessment of the follow-up dose or contrast.

Perform Intervention, Treatment, or Procedure (optional)

Deliver Second Bolus Injection of Intravenous Contrast Agent

Assess the change from the initial patient condition and repeal the process. Note that the same clearance technique may be used at the end of a contrast agent infusion (ml/unit time) to reachieve baseline before proceeding with additional infusions or bolus injections.

METHODS OF ULTRASOUND IMAGING USING ECHOGENICALLY PERSISTENT CONTRAST AGENTS

TECHNICAL FIELD

This invention is in the field of ultrasound imaging. More particularly, it concerns methods of ultrasound imaging using microbubble-containing or generating ultrasound contrast agents. The method can further be characterized as involving the application of ultrasound energy to the imaging field to facilitate multiple dose imaging studies.

BACKGROUND ART

Diagnostic ultrasound imaging is based on the principle that sound waves can be focused upon an area of interest and reflected in such a way as to produce an image thereof. The ultrasonic transducer is placed on a body surface overlying the area to be imaged, and ultrasonic energy in the form of sound waves is directed toward that area. As ultrasonic energy travels through the body, the velocity of the energy and acoustic properties of the body tissue and substances encountered by the energy determine the degree of absorption, scattering, transmission and reflection of the ultrasonic energy. The transducer then detects the amount and characteristics of the reflected ultrasonic energy and translates the data into images.

As ultrasound waves move through one substance to another there is some degree of reflection at the interface. The degree of reflection is related to the acoustic properties of the substances defining the interface. If these acoustic properties differ, such as with liquid-solid or liquid-gas interfaces, the degree of reflection is enhanced. For this reason, gas-containing contrast agents are particularly efficient at reflecting ultrasound waves. Thus, such contrast agents intensify the degree of reflectivity of substances encountered and enhance the definition of ultrasonic images.

Ophir and Parker describe two types of gas-containing imaging agents: (1) free gas bubbles; and (2) encapsulated gas bubbles (*Ultrasound in Medicine and Biology* 15(4):319–333 (1989)), the latter having been developed in an attempt to overcome instability and toxicity problems encountered using the former. Encapsulated gas microbubbles, hereinafter referred to as "microspheres," are composed of a microbubble of gas surrounded by a discrete shell of protein or other biocompatible material. Two such protein-shelled imaging agents are ALBUNEX®, which consists of a suspension of air-containing albumin microspheres, and OPTISON™, which consists of a suspension of perfluoropropane-containing albumin microspheres (both of Molecular Biosystems, Inc., San Diego, Calif.). Other examples of microspheres include surfactant coated protein microspheres (Giddey, WO 92/05806), covalently-crosslinked protein microspheres (Feinstein et al., U.S. Pat. Nos. 4,718,433 and 4,774,958; and Klaveness et al., U.S. Pat. No. 5,529,766); and microspheres with biodegradable synthetic polymer shells (Rossling, et al., U.S. Pat. No. 5,501,863; and Bernstein et al., U.S. Pat. No. 5,611,344).

Microspheres are part of a broader category of contrast agents referred to herein as "microbubble-based contrast agents", or simply "microbubble contrast agents." These types of agents derive at least part of their ability to provide contrast by being capable of supplying a plurality of gaseous microbubbles to the site of imaging. In addition to the free gas microbubbles and encapsulated gas microbubbles described by Ophir and Parker, supra, this class of imaging agents includes emulsions containing chemicals that are in the gaseous state or are capable of becoming gaseous (hereinafter collectively referred to as "gaseous emulsions") prior to or during the application of ultrasound.

A variety of different mechanisms have been utilized to enhance the ability of gas-generating emulsions of volatile liquids to serve as ultrasound contrast agents. One mechanism involves the ability of emulsions of volatile liquids to be stabilized in the liquid state until ultrasound energy is applied at the imaging site, which induces vaporization of the liquid to form microbubbles (U.S. Pat. No. 5,536,489). Another mechanism involves the use of volatile liquids which undergo a phase shift from liquid to gas in vivo upon an increase in temperature to body temperature (U.S. Pat. Nos. 5,558,853 and 5,558,854). Still another mechanism involves the ability to promote microbubble formation in vitro prior to application of the contrast agent by subjecting it to a decrease in pressure (PCT WO 96/40282).

Another type of microbubble contrast agent utilizes solid particles which are capable of carrying gas microbubbles on their surface, or form gas microbubbles upon dissolution in a carrier liquid and/or the bloodstream. See for example, U.S. Pat. Nos. 5,147,631; 4,265,251; 4,657,756; and Australian Patent No. 89/40651.

The first generation of microbubble contrast agents generally involved the use of soluble gases, such as air and nitrogen. However, these contrast agents were shown to be of limited use, because their instability in vivo results in a rapid loss of echogenicity following injection. The instability of these agents necessitates repeated and continuous dosing, which is generally undesirable because of the increased volume of injected gas, as well as the added cost.

Attempts at stabilizing microbubble imaging agents has recently focused on the use of less soluble gases. For example, U.S. Pat. No. 5,413,774 describes the use of at least a portion of gas that has a $S_{gas}/\sqrt{MW_{gas}} \leq 0.0031$, where $S_{gas}$ is the water solubility of the gas and $MW_{gas}$ is the average molecular weight of the gas. Also, U.S. Pat. No. 5,529,766 describes the use of protein microbubbles using low molecular weight fluorinated hydrocarbons or sulfur hexafluoride; and U.S. Pat. No. 5,573,751 describes the use of a variety of different fluorine-containing gases.

Stabilization of microbubble contrast agents has greatly improved their overall efficacy for certain applications. For example, one type of ultrasound imaging study involves the use of microbubble contrast agents to trace the flow of blood through the microcirculation. This type of study relies on the ability of certain types of contrast agents, called "tracer agents," to mimic the flow of blood cells through the microcirculation, and also requires that they be stable enough to survive the transit through the microcirculation. However, this application is not easily performed with microbubbles that are stable enough to survive multiple passes through the microcirculatory system under investigation. This is because the study of microcapillary circulation depends on the ability to determine the echogenicity of the microcapillaries during the first pass of the contrast. Hence, accumulation of the contrast agent with each pass makes it difficult to determine the relationship between echogenicity after administration and the amount of contrast agent which was administered.

In addition to having increased in vivo persistence, certain stabilized contrast agents also have a tendency to become preferentially lodged in various tissues or in the microcirculation. These types of contrast agents are sometimes called "depot agents." Examples of depot agents include: Quantison Depot®, (Andaris, Nottingham, England); and EchoGen®, (Sonus, Bothell, Washington; See *Journal of the American Society of Echocardiography,* 10(1):11–24 (1997)). Although less useful for studying blood flow, depot agents can thus have the added benefit of localized enhancement of ultrasound images. For this reason, many ultrasound contrast agents are designed specifically as depot agents through the use of targeting moieties which cause them to become concentrated at a desired imaging site. See, for example, PCT WO 94/08627. However, such targeted contrast agents can have the disadvantage of maintaining persistent echogenicity at the target site for such a long duration that their prolonged presence interferes with the ability to perform subsequent imaging studies with a second dose of contrast agent (i.e. a multiple dose imaging study). Furthermore, depot agents may exhibit toxic side effects if they obstruct the microcirculation for an undue length of time.

It has recently been reported that prolonged exposure to ultrasound energy can rapidly diminish the echogenicity of microbubble contrast agents after administration (Vandenberg and Melton, *J. Am. Soc. Echocardiogr.* 7:582–589 (1994)). In an attempt to circumvent this problem, Porter has described that the destructive effects of ultrasound can be avoided by limiting the exposure of the microbubble contrast agents to ultrasound energy after injection (U.S. Pat. No. 5,560,364). Although for most applications, the effects of exposure to ultrasound energy are considered to be undesirable, it has previously been reported that for at least one type of imaging study, the effects of ultrasound energy on echogenicity can be used beneficially. In particular, it was reported that during an imaging study of the myocardium involving a continuous venous infusion (a single dose imaging study) of a microbubble imaging agent, application of ultrasound energy to the myocardium can be used to temporarily eliminate echogenicity of the contrast agent in order to assess reperfusion of the contrast agent back into the myocardium (Wei et al., *JACC* 29(2):1081–1088 (1997)). However, previous reports have not been identified that describe the use of increased exposure of microbubble contrast agents to ultrasound energy to facilitate multiple dose imaging studies.

Many different imaging studies call for the administration of two or more doses of ultrasound contrast agent. For example, when a patient is undergoing a stress echocardiogram, whether pharmacological agents or mechanical exercise is used as a stressor, it is necessary to initially obtain an ultrasound image of the patient at rest, in the presence of contrast agent, then subject the patient to the stress, and obtain a second diagnostic image or images at peak stress. These studies are designed to assess such conditions as reversible ischemia, exercise induced angina or unstable angina. Stress echocardiography employs either no ultrasound contrast agents or ALBUNEX® contrast agent (Molecular Biosystems, Inc., San Diego, Calif.) for enhancing the assessment of wall motion defects that follow myocardial ischemia Currently, several ultrasound contrast agents are in clinical trials for use in a method of assessing myocardial perfusion status. In these studies, ultrasound is used after injection of a contrast agent at rest, followed by an inducement of stress, and then by a second injection of contrast agent during peak stress. Because the "at rest" and "peak stress" injections are often given very close together, there may be an interference in the myocardial echogenicity after the second dose due to persistent echogenicity from the first dose. This results in the inability to obtain useful information from the second injection.

As described above, the persistence of echogenicity from a first dose of a microbubble contrast agent can interfere with subsequent imaging studies utilizing a second dose. Such interference of residual ultrasound tissue enhancement from previous doses of contrast agents could be described as a nuisance or a confounding factor in the accurate assessment of changes in tissue perfusion status over the course of a study. The researcher or clinician, using visual assessments of gray scale brightness or more quantitative methods of densitometry, may not be able to discern ultrasound contrast in the tissue as resulting from pre or from post intervention for example.

It is therefore an object of the present invention to provide a method of imaging which allows for a first dose of a microbubble contrast agent to be quickly and effectively "cleared" from the imaging field so that a second dose can be administered and a second imaging study performed which is free from interference due to the persistence of the first dose. This allows clinicians to use echogenically persistent microbubble contrast agents to enhance ultrasound intensity without the associated interference with subsequent imaging studies after additional administration of contrast agent. Utilizing this method, the clinician is able to capture ultrasound images derived from a first administration of contrast agent during any phase of its echogenic effect on the imaging site. After completion of the initial imaging study, the clinician is able to efficiently eliminate residual echogenicity so that subsequent imaging studies which may follow surgical intervention or treatment can be immediately performed without interference.

DISCLOSURE OF THE INVENTION

The present invention relates to a method of performing a multiple dose ultrasound imaging study of a site within a mammalian subject. It is particularly useful when employing a persistent contrast agent, such as a microbubble contrast agent, to maximize contrast, but the persistence interferes with subsequent imaging. The steps involved in the method of the present invention are as follows: first, the ultrasound image(s) of a given site is(are) obtained after administration of a first dose of contrast agent at a first energy level; second, the energy level is increased to eliminate the echogenicity from the first dose of contrast agent (i.e. the echogenicity of the site is returned to the pre-contrast level); and lastly, the ultrasound image(s) is(are) obtained following administration of a second dose of contrast agent.

Although the method is generally useful when employing a microbubble contrast agent, it may also be used whenever a contrast agent is employed whose echogenicity can be reduced by applying ultrasound energy. In a preferred embodiment, the method utilizes protein shelled microspheres as the imaging agent. The microspheres may contain any gas or gas mixture, although insoluble gases such as perfluoropropane are preferred over soluble gases such as air. A particularly preferred microsphere is one formed from a mixture of a soluble gas and a vapor of a volatile liquid, such as perfluoropentane or perfluorohexane. In particular, microspheres which are formed from a ratio of either 50% air/50% perfluoropentane vapor (v/v) or 85% air/15% perfluorohexane vapor are especially preferred.

In addition to microspheres, the imaging agent which is used in the practice of the method of the present invention may also be an emulsion, preferably one containing a perfluorocarbon, such as perfluoropentane or perfluorohexane.

Since the method of the present invention is most useful when the imaging site is such that persistent echogenicity is expected, the method of the present invention is particularly useful when imaging microcapillary beds where the flow of imaging agents through and eventually out of the field of imaging is somewhat slow.

The method of the present invention relies on the ability to increase the ultrasound energy to a site of imaging to hasten the elimination of echogenicity from a contrast agent. Such increase in energy can take a variety of different forms. For example, ultrasound energy can be increased by any of the following means, either alone or in combination with one another: changing from intermittent imaging to continuous imaging; increasing the power level; lowering the frequency or changing from B-mode to color doppler mode.

BRIEF DESCRIPTION OF THE DRAWINGS

FIG. 1 depicts a flow chart which describes the steps of a representative embodiment of the present invention.

MODES FOR CARRYING OUT THE INVENTION

Figure 2:
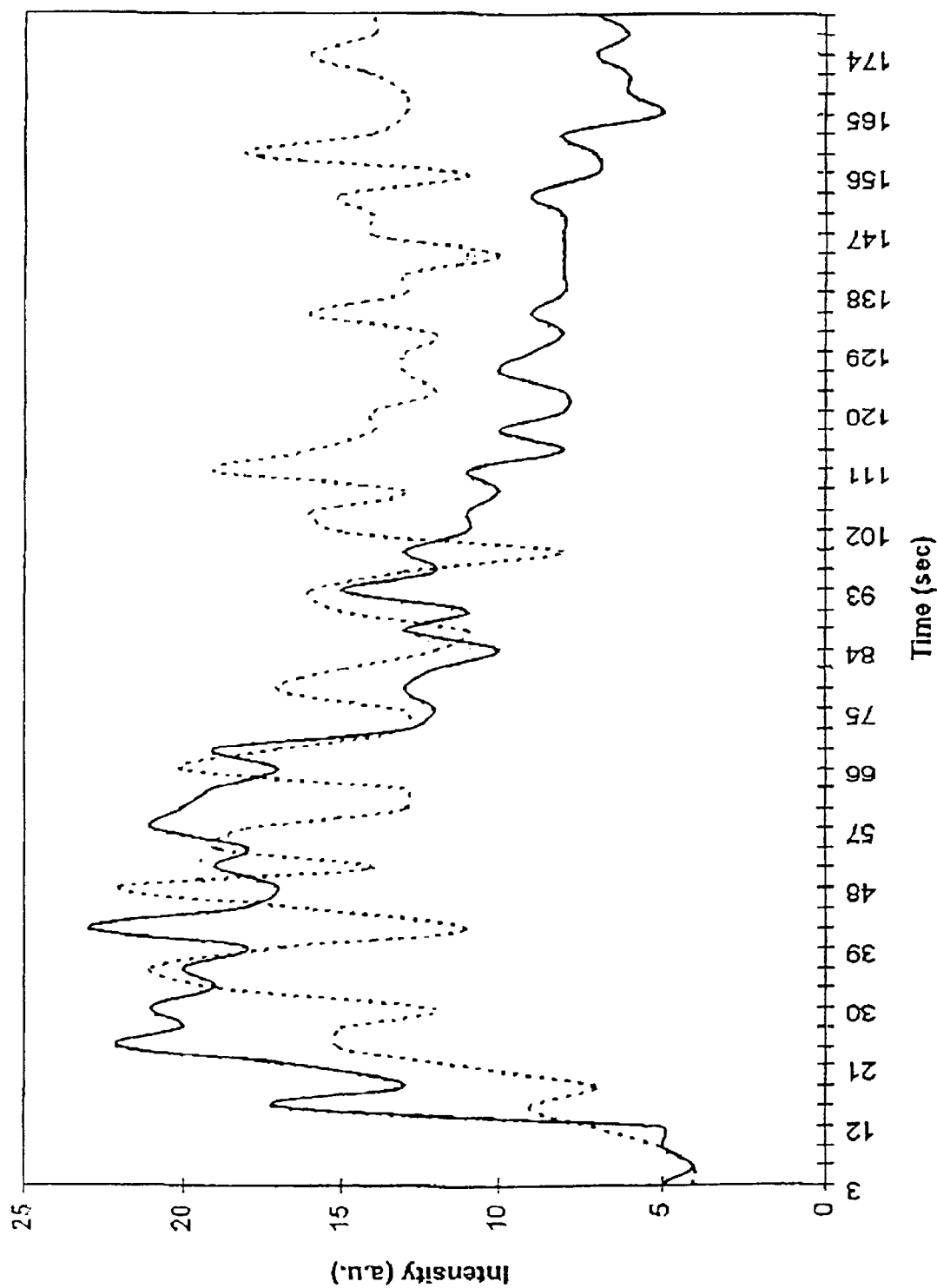
FIG. 2 depicts the changes in acoustic densitometry time-intensity curves of the mid ventricular septum (____) and the left ventricular chamber (____) at 10% transmit power following intravenous administration of protein microspheres made from a 1:1 mixture of air:perfluoropentane vapor.

The present invention provides a method of imaging using multiple doses of an echogenically persistent microbubble imaging agent. In particular, the present invention provides a method of imaging comprising performing a first imaging study of a target site after a first dose of contrast agent, applying a sufficient amount of ultrasound energy to eliminate any residual echogenicity attributed to the first dose, then performing a subsequent imaging study of the target site after a second dose of contrast agent.

The method of the present invention is particularly useful when an echogenically persistent contrast agent is required to achieve a certain degree of image enhancement, but subsequent contrast agent-enhanced imaging studies are also contemplated and cannot be carried out until after the echogenicity attributed to the first administration has subsided. In this regard, the invention is useful whenever the contrast agent which is initially administered remains echogenic at the imaging site longer than the desired length of time between imaging studies.

The in vivo stability, echogenic properties and target specificity which define the echogenic persistence of ultrasound contrast agents that are currently being utilized for diagnostic imaging are known. Hence, the echogenic persistence at the imaging site will be predictable for most imaging agents. However, when the echogenic persistence of an imaging agent which is contemplated for use in a multiple dose imaging study is not known, it may be useful to determine whether interference from the first dose is expected, in which case the method of the present invention would be useful.

Typically, a contrast agent which is stabilized will exhibit undesirable echogenic persistence. A contrast agent is considered "stabilized" if it is both pressure resistant and long-lived in vivo. To make an in vitro determination of whether a contrast agent is stabilized, echogenicity of the contrast agent is determined after exposure to conditions which mimic the in vivo environment that it will be subjected to after administration and during performance of the first imaging study. Accordingly, a contrast agent is too stable to perform multiple dose imaging studies if, during the length of time it would take to perform the first imaging study, plus the length of time desired between studies, it is still echogenic. This means that if the contrast agent remains echogenic for too long after application of a constant pressure of 150 mmHg (the constant systolic pressure), and is additionally stable to transient exposure of up to 390 mmHg (150 mmHg plus the transient intracardiac pressure during systole of 250 mmHg, and the momentary pressure caused by sonic compression, which has been reported to be 140 mmHg (see U.S. Pat. No. 5,540,909)), interference from the first dose during the second imaging study might be expected. Also, since the effects of pressure on a population of microbubble contrast agents depends on the concentration of the microbubbles, any in vitro determinations of stability of the microbubble contrast agent should account for dilution upon administration, as well as localized concentration due to depot effects. In addition, stability studies should be performed at in vivo temperatures and in dilutents with gas concentrations that approximate blood to more closely approximate in vivo conditions. If in vitro information is unavailable or impractical to obtain for the clinician, the baseline condition can be compared to post injection to determine the need for the claimed procedures. On most of the available ultrasonographs a baseline freeze frame or cineloop (movie clip) can be stored before the first injection and then compared visually or with densitometry to the post injection freeze frame or cineloop side by side for ease of comparison. If the vascular bed appears enhanced compared to baseline, when a new injection is desired for diagnostic purposes, the present invention may then be employed.

In addition to stabilized contrast agents, depot agents may also exhibit undesirable echogenic persistence at the imaging site because of their propensity to accumulate at the target site.

The contrast agents which are useful in the method of the present invention are contrast agents which contain or are capable of generating microbubbles (i.e., "microbubble contrast agents"), since the echogenicity of microbubble contrast agents is susceptible to the application of ultrasound energy, i.e. the application of ultrasonic energy diminishes echogenicity. This also includes microbubble contrast agents whose echogenicity may be initially enhanced by applying ultrasound energy in vivo (See U.S. Pat. No. 5,536,489 and U.S. Pat. No. 5,540,909), but is subsequently diminished as the application of ultrasound energy continues.

General Description of Microbubble Contrast Agents

Microbubble contrast agents can take a variety of different forms, all of which can be easily prepared using known methods. For example, they may take the form of free gas microbubbles surrounded by a stabilizing liquid carrier; microbubbles encapsulated by solid shells, i.e. "microspheres"; emulsions of surfactants and gases and/or volatile liquids that become gaseous at some time during the imaging procedure; and particles that entrap or carry gases and/or volatile liquids that form microbubbles upon dissolution in a liquid carrier and/or in vivo.

"Free gas microbubbles" refers to suspensions of microbubbles which are dual component systems. In other words, they consist only of the gas within the microbubble and the surrounding solution which interacts at the gas-liquid interface to stabilize the microbubble. In general, free gas microbubbles are considerably less stable than more complex system that include organized layers of biomaterials or solid shells surrounding the microbubble. However, certain free gas microbubble-containing contrast agents which employ relatively insoluble gases (compared to air)

are so stable that their echogenic persistence at the site of imaging would be expected to interfere with subsequent contrast enhanced studies, thus necessitating the use of the method of the present invention. For example, in U.S. Pat. Nos. 5,393,524; 5,409,688; 5,558,854; and 5,558,094, free gas microbubble contrast agents are described that may last as long as 99 minutes.

Microspheres are characterized by the presence of solid shells surrounding the microbubbles of gas. The microsphere shells may be composed of a variety of a biocompatible materials which are capable of forming a thin layer around a microbubble of gas. Such materials are usually polymeric at the time of microsphere formation, or they may be monomeric to begin with, and subsequently polymerized during microsphere formation.

Suitable polymers can include proteins, carbohydrates, lipids, synthetic polymers or combinations thereof. Such polymers and the formation of microspheres therefrom are well known in the art and exemplified by those described in U.S. Pat. Nos. 4,957,656; 5,137,928; 5,190,982; 5,149,543; 5,527,521; 5,529,766; 5,562,893; and 5,578,292. As described therein, the polymers and thus the shells formed therefrom may be additionally stabilized by crosslinking during or after microsphere formation. Additionally, the selection of the gas is also reported to influence microsphere stability. Accordingly, any previously described microsphere containing a soluble gas may be stabilized by substituting an insoluble gas such as a C1–C6 perfluorocarbon for the air.

Another type of microbubble imaging agent is an emulsion which is generally characterized by a continuous aqueous phase containing surfactants, and a dispersed gas phase, or a dispersed gas-forming liquid phase. For example, see U.S. Pat. Nos. 5,558,853 and 5,558,855.

Liposomes have also been described as being useful as microbubble contrast agents. Although in some respects liposomes are similar to microspheres in that they have layers with discrete properties, they are also somewhat like emulsions in that the layer-forming lipids have surfactant properties. In any event, liposomes which are useful in ultrasound imaging are described in PCT Applications WO 91/09629 and WO92/17212.

Microparticles which entrap or carry gases or gas-forming chemicals are also useful in the present invention. For examples of such, see PCT Application WO 91/12823, and U.S. Pat. No. 5,147,631.

The maximum size (mean diameter) of the microparticle is defined by that size which will pass through the pulmonary capillaries. In the case of humans, that size will typically be less than about 10 micrometers. Correspondingly, the minimum size is that which will provide efficient acoustic scattering at the ultrasonic frequencies typically used for ultrasound imaging. (The frequency may vary with the mode of imaging, e.g., transthoracic, transesophageal, and will normally be in the range of 2–12 MHz). The minimum size will typically be about 1 microns. Accordingly, the typical size range of the microparticles used in the invention method will be about 1 to about 10 micrometers, more usually 2 to 6 microns. Microsphere size can easily be determined using known methods, such as with a Coulter Multisizer II particle counter/sizer (Coulter Electronics, Hialeah, Fla.).

Gases or Gas-Forming Chemicals

The microparticle core material in the microbubble contrast agents of the present invention can be a gas and/or a liquid, which intends that it comprises a gas, a liquid, a mixture of gases, a mixture of liquids, or a mixture of gas(es) and liquid(s). Suitable core material must also be pharmacologically acceptable, i.e. biocompatible and having minimal toxicity. The term "biocompatible" means the ability of the gas (or liquid) to be metabolized or eliminated in-tact without the formation of toxic byproducts. Examples of such suitable core material are well-known in the art. See, for example, U.S. Pat. No. 5,409,668 which discloses the use of free gas microbubbles as in vivo imaging agents, any of which could be used as core material in the contrast agents which are useful in the methods of the present invention.

In general, suitable core materials include soluble gases such as air, carbon dioxide, nitrogen, oxygen, nitrous oxide, hydrogen, carbon dioxide, helium, argon, xenon, methane, ethane, propane, n-butane, isobutane, pentane; and insoluble gases (having a solubility less than 0.01 mL/mL of water under standard conditions) such as sulfur hexafluoride and the C1 to C6 perfluorocarbons; suitable liquids are those that are liquid when administered, but that became gaseous after administration, such as perfluoropentane or other halogenated higher molecular weight hydrocarbons. Particularly preferred are gas-liquid mixtures, for example those found in microspheres made from a mixture of air or a low boiling point (gaseous) perfluorocarbon such as perfluoropropane, and a vapor of a high boiling point (liquid) perfluorocarbon such as perfluoropentane, perfluorohexane or perfluoroheptane. Although the ratio of gas to vapor used to form microspheres can be varied to achieve a desired stabiltiy, a ratio of 50% air to 50% perfluoropentane (v/v) or a ratio of 85% air to 15% perfluorohexane has been shown to be particularly useful.

The Site of Imaging

The present invention is most useful when the site of imaging comprises a vascular bed, in which capillary flow is approximately 0.1 to 2.0 mm/sec, i.e. the typical value in resting humans (see, e.g., Schrope et al., *Ultrasound Imaging* 14:134–158 (1992)). For imaging sites comprising large vessels with relatively rapid flow such as the aorta, carotid arteries and cardiac chambers (without consideration of the myocardium), the subject invention would not be needed because the persistence of echogenicity of a contrast agent would be expected to be rapidly cleared from the imaging field. Accordingly, the present invention is best used for imaging organs containing microcapillary beds, including but not limited to the myocardium, kidney, liver, spleen, prostate, breast tissue, etc.

Performing the Imaging Study

1. Preparation and Administration

The microparticles are prepared and administered using known methods. For example, they may be prepared as a suspension in a sterile, aqueous, injectable carrier such as saline or a protein solution. Such carriers are well known in the pharmaceutical formulation art. The concentration of microparticles in the suspension will normally be in the range of $1 \times 10^7$ to $1 \times 10^{10}$, more usually $1 \times 10^8$ to $1 \times 10^9$, per mL of suspending medium. In such use, the suspension is generally injected into a peripheral vein at about 0.05 to 0.5 cc per kg body weight.

For the practice of this invention, the contrast agent preparation can be delivered either in a bolus or as an infusion, but the key is that the delivery of the previous injection is discontinued once initial ultrasound image(s) for diagnostic information is(are) obtained. Then, following another injection or infusion of contrast agent is used to generate more ultrasound images without interference from the previous injection of contrast.

2. Acquiring the Images

The present invention can easily be practiced by skilled ultrasonographers by following the manufacturer's instructions for the initial set up to acquire baseline images. Regarding the power settings to be used, general practice of ultrasound imaging specifies that for the safety of the patient, the acoustic power outputs should be set at As Low As Reasonably Achievable, or the ALARA principle. The power output generated can be judged in the most recent sonograph models by the on-screen standard display of Mechanical Index (MI) in B-modes or with Thermal Index (TI) in Doppler modes. For the purposes of this invention, the MI is the most useful parameter. The MI is used to standardize patient exposure to ultrasound and is a calculated parameter done by the instrumentation manufacturers specifically for each probe or transducer available. The MI is mathematically defined as follows:

$$MI = \frac{\text{Peak Rarefaction Pressure}}{\sqrt{\text{Frequency}}}$$

In general, the power setting for the contrast ultrasound imaging should be kept as low as possible while still being able to generate a useful image. The overall gain settings on most ultrasonographs, and post processing software choices can be adjusted by a trained sonographer to compensate for the low power settings. Once the initial image of the target organ is established, it is useful to store a baseline image either in the ultrasonograph memory for freeze frame or cineloop comparison, or if this capability is not available, a short video tape sequence of baseline imaging can be used for future referral. The contrast agent is then either infused or injected in a bolus, intravenously or intra-arterially (via a catheter), at dosages recommended by the manufacturer to achieve tissue perfusion or accumulation at the tissue site, depending on the type of agent utilized. The peak enhancement to be used for diagnosis is then recorded using any available method. (For narrative descriptions of the visual appearance of contrast enhancement in the myocardium as an example, please see Examples 3–5). For three dimensional imaging, the injection of contrast and the power settings principles are essentially the same, but the equipment and timing of images may differ.

After allowing the imaging agent to accumulate at the target site, ultrasonic energy is applied to the tissue/organ to be imaged and reflected energy is collected and translated into an image using any ultrasound imaging equipment. Two dimensional (2-D) or multidimensional (e.g. three-dimensional (3-D)) ultrasound equipment and procedures may be used to acquire the image. Such procedures and equipment are conventional.

3. Eliminating Residual Echogenicity

After completing the first imaging study, the residual level of contrast can be determined either visually or using densitometric methods by comparing the baseline stored images, freeze frame, cineloop or video tape to the current images. If the vascular bed of interest is determined to be more echogenic than the baseline level, the residual echogenicity can be eliminated by increasing the ultrasound energy administered to the imaging site. Delivered ultrasound energy is defined as the strength and exposure time of an area in the ultrasound beam. The ultrasound energy level can be increased, for example, using any of the following means either alone or in combination.

(a) Switching the pulse acoustic output from the transducer from intermittent mode to continuous mode: Typically in intermittent or continuous response mode the ultrasound interrogation acoustic pulses are either gated or triggered to one point in the cardiac cycle using the EKG and can be manually switched on and off. The resulting ultrasound pulse frequencies are usually at approximately 1 Hz as compared to continuous B-mode (in which the lowest rates are approximately 30 Hz and can be increased for improved image resolution). Thus, the intermittent modes typically results in 30 times less or smaller power exposures to the tissue and agent than are present in continuous modes.

(b) Increasing the amount of power applied to the imaging field from the low setting to a higher power setting: The higher the power, the faster the contrast effect will be cleared. As detailed in Example 5, the power setting can be increased by increasing the acoustic output (increasing the dB output level) and the contrast effect will disappear within 30 seconds. Typically MI values of 0.1 to 0.6 or higher are clinically useful in human subject.

(c) Lowering the imaging ultrasound frequency: Lower frequency ultrasound waves penetrate or propagate deeper in tissues and thus result in larger peak rarefaction pressures deeper in the tissues than can be achieved with higher frequencies. It is the intensity of the pressure waves generated by ultrasound in tissues that is related to the loss of echogenicity of microbubble-based contrast agents.

(d) Switching from B-mode to Color Doppler modes and sweeping the color box across the imaging area: The amount of ultrasound energy as measured for spatial peak temporal average (SPTA) in Color Doppler modes can be as high as 2000 m W/cm$^2$ as compared to typical cardiac phased array transducers where the SPTA average maximum is approximately 240 m W/cm$^2$ (Kremkau, Diagnostic Ultrasound, WB Saunders, Philadelphia Pa. (1993)). Thus, Doppler mode effectively delivers more acoustical power than typical B-mode.

4. Performing a Second Imaging Study

Once the residual echogenicity has been eliminated, steps 1 and 2 can be repeated without interference from the echogenicity of the first dose.

EXAMPLES

Example 1

Protein Microspheres Stabilized by Perfluoroalkane Vapors

One type of microsphere which is useful in the method of the present invention consist of gas cores encapsulated by heat-insolubilized protein, which are formed in the presence of heated perfluorocarbon vapors. The perfluorocarbon preferably has a relatively high boiling point, i.e. above 20° C. at standard pressure. Perfluoropentane, perfluorohexane and perfluoroheptane are preferred. The term "vapor" intends the gaseous phase of a liquid which may be formed by raising the temperature of the liquid above its boiling point. The heated perfluorocarbon vapor interacts with the shell-forming protein during formation and subsequent cooling to render the resultant microsphere shell less permeable to the aqueous exterior. This helps to prevent contact between the internal gas core and the surrounding aqueous environment, which protects the gas from becoming solubilized in the aqueous environment, especially when the gas core comprises a soluble gas. The effects of loss of the gas core due to solubilization is observed as pressure instability. Microspheres thus formed exhibit pressure resistance beyond that expected for an equivalent microsphere which is not formed in the presence of a heated perfluorocarbon vapor.

The protein shell-forming material which is useful in forming these microspheres includes both naturally occurring filmogenic proteins, proteins made by methods involving recombinant DNA, and chemically synthesized proteins and amino acid polymers, which are collectively referred to herein as "proteins." Suitable proteins must be able to form a shell or film around the core material when the protein is insolubilized.

Examples of naturally occurring proteins include gamma-globulin (human), apo-transferrin (human), β-lactoglobulin, urease, lysozyme, and albumin. Human serum albumin is a preferred shell material. Chemically synthesized amino acid polymers which are useful in the present invention can optionally be in the form of block or random co-polymers combining both hydrophobic and hydrophilic amino acids in the same or different amino acid chains. Albumin is preferred, and more particularly human serum albumin.

Protein-shelled microspheres are made by any known method, such as subjecting a mixture of an aqueous solution of a heat-insolubilizable protein and the gas-vapor mixture to mechanical or ultrasonic cavitation as described in U.S. Pat. Nos. 4,844,882; 4,957,656; and 5,552,133.

These microspheres exhibit unexpectedly enhanced pressure resistance when compared to microspheres with a core of a soluble gas. If microspheres are prepared with 50% air and 50% of perfluoropentane vapor (v/v) as the gas phase, these microspheres would be expected to exhibit the same resistance to a pressure of 10 psi for equivalent samples of approximately $1 \times 10^7$ microspheres per mL. This is because the solubility of air in the core, or diffusion through the shell, would not be expected to be diminished by the presence of the perfluorocarbon. Accordingly, microspheres made with the same amount of air would be expected to lose the air fraction after being subjected to sufficient pressure to solubilize only the air fraction, and suffer partial destruction. However, the microspheres made with air-perfluorocarbon vapor mixtures exhibit resistance to pressure.

Example 2

Protein Microspheres Stabilized by "Tanning"

Another type of microbubble contrast agent which is useful in the present invention comprises protein microspheres surrounding a core of gas, liquid, or a gas/liquid mixture, whose stability has been enhanced by treating the protein shell with a metal salt. This causes formation of polynuclear coordination complexes between the ionized carboxyl groups of the surface-exposed amino acids and bridging ligands. The preferred metals are chromium, zirconium, titanium and aluminum. The process parameters may be varied in order to achieve the desired amount of tanning over any given period of time. The degree of tanning is dependent upon the concentration of the metal salt, duration and temperature of the reaction. The preferred concentrations of metal salt solutions generally range from 1–30 mM with temperatures of up to approximately 160° C. for a few minutes to several hours or more. The tanned microspheres can be further processed in order to hydrophilize the shell to increase circulation times and/or to attach targeting moieties which have a specific affinity for certain organs or cell types.

The resulting microspheres are capable of traveling through the capillary system. The enhanced stability results in their ability to accumulate at a particular site for enhanced echogenicity. Furthermore, the longevity of the microparticles aids in the ability to perform organ perfusion studies.

"Tanning" refers to the use of metal salts such as chromium III potassium sulfate to form polynuclear coordination complexes between the ionized carboxyl groups of the surface-exposed amino acids, and bridging ligands such as hydroxol, oxo and sulfato groups. Other salts for tanning microparticles such as sulfates of zirconium, titanium and aluminum may also be used. Accordingly, suitable shell-forming proteins material must also exhibit free carboxyl groups on the surface of the microparticles and be capable of forming such coordination complexes.

Tanned microspheres can be distinguished by their increased stability and longevity both in vitro and in vivo. For example, tanned air-containing microspheres are some 20–40 times more stable (i.e. remain echogenic) than untanned air-containing microspheres, and may remain echogenic in vivo for 8 minutes or more. Tanned microspheres which contain less soluble gases such as perfluoropropane, or gas-vapor mixtures such as air and perfluorohexane would be expected to last even longer.

Example 3

Pre-Injection Imaging

Prior to the injection of the contrast agent a B-mode fundamental ultrasound image of the heart was obtained. For the examples, a 5 MHz phased array transducer connected to a Hewlett Packard Sonos 2500 (Hewlett Packard, Boston, Mass.) ultrasonograph was used, but similar results can be obtained with power output/MI matching at 3.5 MHz or 2.7 MHz, and other frequencies on other instruments including but not limited to ATL HDI 3000 and Toshiba Power Vision. The cardiac ultrasound image was optimized and maintained constant using standard clinical procedures with the exception of the power output parameter which will be discussed in detail for each desired end point. Any cardiac ultrasound view may be used, but for the purposes of the description to follow a parasternal short axis view imaging through an intact chest wall, at the level of the papillary muscles, was the image plane. The parasternal short axis image is approximately a midpoint cross sectional view plane of the heart which appears, at baseline or precontrast, on a monograph video screen as a medium gray oval on its side (representing the left ventricle), containing a very dark gray circle in the right portion of the oval and a very dark gray crescent on the left end of the oval (representing the right ventricle). The left ventricular chamber appears at baseline as the dark gray roughly circular structure and the right ventricular chamber is the dark crescent structure. The myocardium is the mid gray portion of the oval, which includes the ventricular septum separating the two chambers.

Example 4

Post-Injection Imaging

Albumin microspheres containing perfluoropropane as the encapsulated gas were prepared according to U.S. Patent No. 4,957,656 (referred to herein as "PF3 microspheres"). An anesthetized canine was instrumented with silastic catheters in the femoral artery and vein and placed in an approximately left lateral decubitus position on a standard surgical table. Standard bolus injection of PF3 microspheres between 0.5 and 3 cc intravenously was injected at both low power MI 0.2 (10% power output on a maximum range of 40 dB) and high power MI 0.6 (80% power) (These particular data from Preclinical dog number #95). Visual images on the ultrasonograph followed a typical sequence described as follows: The volume of the test agent was flushed rapidly into the vein of the canine with approximately 5 mL saline bolus delivered with a 10 cc syringe attached to a stopcock. The contrast agent appeared in the right ventricular chamber within a few seconds and appeared bright followed immediately by a black shadow (ultrasound beam attenuation). A bright margin remained at the top (proximal to the transducer) of the crescent shaped right ventricular chamber. Within several heart beats white contrast material appeared to swirl into the left ventricular chamber filling it completely. A wedge shaped dark shadow (attenuation) then appeared in the lower (distal to the ultrasound source) portion of the cardiac image. The left ventricular filling or opacification (LVO) was followed by a brightening of the gray color of the myocardium as it filled the myocardial vasculature from the coronary arteries (myocardial enhancement or MCE). At this stage the increased brightness of the myocardium could only be seen the most proximal areas of the heart muscle to the ultrasound source because of the attenuation (shadow) from the heart chambers. The attenuation in both right and left chambers lasted several seconds, then dissipated leaving the ventricle and the myocardium appearing as very light gray (isointensity on a gray intensity scale in the early phase). The myocardium appeared as a much brighter than the baseline image. The contrast agent appeared to empty (darkening of the gray) first from the myocardium then the left ventricular chamber.

Left ventricular attenuation or shadowing was similar at the two power settings and the brightness or enhancement for the myocardium was similar (somewhat brighter for the higher power setting). The major power effect for PF3 microspheres injection was a relatively minor duration change (38 seconds at 10% power to 23 seconds at 80% power) of the myocardial enhancement effect at lower power setting in continuous mode (30 Hz). Changing the power setting had a greater effect in harmonic mode for both myocardial enhancement brightness for PF3 microspheres and duration compared to fundamental. In harmonic mode the fundamental frequency 1.8 MHz to observe the harmonic at 3.6 MHz results in more energy penetration to the contrast agents, and thereby a magnification of the destruction rate of PF3 microspheres echogenicity or the visual maintenance of bright light gray images (also true for other harmonic pairs studied up to 2.5/5.0 MHz). For OPTISON™ cardiac perfusion imaging brightness and duration of the contrast effect in harmonics can be altered primarily by using intermittent triggering. Altering the power settings does lengthen the contrast effect, however, in every case the profile of the contrast effect from a bolus injection remains the same (e.g., in order of occurrence: left ventricular filling, LV attenuation, myocardial enhancement, disappearance of the myocardial enhancement, and finally disappearance of the enhancement in the left ventricular chamber).

Manipulation of power with PF3 microspheres does not change the order of the above events, and all occur at any power setting, only duration and intensity of the contrast effect is altered by changing the acoustic power output.

Example 5

Residual Echogenicity

An anesthetized canine was instrumented with silastic catheters in the femoral artery and vein and placed in an approximately left lateral decubitus position on a standard surgical table. The image was optimized at 10% of the power output of the HP2500 using a 5 MHz transducer (MI 0.2). Similar effects can be achieved by changing the settings with other instruments and other frequency transducers. The key is to match the instrument setting to achieve a power output based on the contrast outcome desired. The following visual image was obtained using the procedure outlined: The test agent was uniformly suspended within the original vial by rolling and inverting the vial until the article was visually identical in all parts of the liquid volume. A volume (generally 0.5 mL) of the suspension was drawn into a 3 cc syringe using an 18 gauge hypodermic needle. The needle was removed and the volume loaded into the saline filled femoral venous catheter using a 3-way stopcock. The volume of the test agent was flushed into the vein of the canine with a rapid approximately 5 mL saline bolus delivered with a 10 cc syringe attached to the stopcock. The contrast agent first appeared in the right ventricular chamber within a few seconds and first appeared bright white followed rapidly by an intense black shadow (ultrasound beam attenuation) except for a bright white margin at the top (proximal to the transducer) of the crescent shaped right ventricular chamber. Within several heart beats white material appeared to swirl into the left ventricular chamber, first filling it completely (LVO), then producing a wedge shaped dark shadow in the lower (distal to the ultrasound source) portion of the cardiac image. The contrast agent substantially brightened the myocardium as it filled the myocardial vasculature from the coronary arteries (MCE). As before, the increased brightness could only be seen at this stage in the most proximal areas of the heart muscle to the ultrasound source because of the attenuation (shadow) from the heart chambers. The attenuation in both right and left chambers lasted several seconds, then dissipated leaving the ventricle and the myocardium very light gray (bright). In this early phase, the brightening of the left ventricular chamber was equal (isodensity on a gray scale) to the myocardium filled with contrast agent. The myocardium appeared much brighter than the baseline image. The contrast agent appeared to empty from the chambers as first the right ventricular chamber then the left ventricular chamber darkened with time (leaving the myocardium bright). At approximately 3 to 5 minutes post injection the left ventricular chamber appeared as a darkened gray circle surrounded by a light gray, "doughnut shaped" myocardium as the contrast agent persisted in the myocardial vasculature, but not in the left ventricular chamber. As depicted in FIG. 2, there is persistent above-baseline echogenicity in the myocardium. The brightness of the myocardium faded with time returning to the baseline (medium gray) approximately 20–45 minutes following the intravenous bolus injection of the contrast agent.

Example 6

Eliminating Residual Echogenecity

Once the myocardial contrast effect is no longer needed, or a researcher wishes to return the myocardium to baseline contrast intensity for the purposes of reinjecting contrast for further image collection, previous myocardial enhancement is terminated as follows: Either increase the b-mode power setting to a higher percentage output (or increase the dB level), put on color flow Doppler and sweep the window across the myocardial image plane for 1–2 minutes, switch from intermittent to continuous or switch to a lower frequency or to Color Doppler mode. This will effectively return the myocardial contrast induced intensities back to baseline or precontrast.

Modifications of the above-described modes for carrying out the invention that are obvious to persons of skill in the field of ultrasound contrast agents are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of performing a multiple dose ultrasound imaging study of a site within a mammalian subject comprising the steps of:
   a) generating an ultrasound image of the site after administering a first dose of a microbubble ultrasound contrast agent by applying ultrasound at a first energy level;
   b) eliminating echogenicity from the first dose of the microbubble ultrasound contrast agent by applying ultrasound at a second energy level, wherein the second energy level is greater than the first energy level; and
   c) generating an ultrasound image of the site after administration of a second dose of a microbubble ultrasound contrast agent.

2. The method of claim 1, wherein the microbubble contrast agent comprises protein shelled microspheres.

3. The method of claim 2, wherein the microsphere contains air.

4. The method of claim 2, wherein the microsphere contains air and perfluoropentane.

5. The method of claim 2, wherein the microsphere contains air and perfluorohexane.

6. The method of claim 1, wherein the microbubble contrast agent comprises an emulsion.

7. The method of claim 6, wherein the emulsion comprises perfluorocarbon.

8. The method of claim 1, wherein the site of imaging includes a microcapillary bed.

9. The method of claim 1, wherein the ultrasound energy applied in step a) is intermittent, and the ultrasound energy applied in step b) is continuous.

10. The method of claim 1, wherein the ultrasound energy applied in step a) is at a first power level, and the ultrasound energy applied in step b) is at a second power level, wherein the second power level is greater than the first power level.

11. The method of claim 1, wherein the ultrasound energy applied in step a) is in B-mode, and the ultrasound energy applied in step b) is in color doppler mode.

12. The method of claim 1, wherein the ultrasound energy applied in step a) is at a first frequency, and the ultrasound energy applied in step b) is at a second frequency, wherein the second frequency is less than the first frequency.

* * * * *